United States Patent
Ino et al.

(10) Patent No.: US 6,190,637 B1
(45) Date of Patent: Feb. 20, 2001

(54) METHOD FOR PREPARING [F-18-]FLUORIDE ION

(75) Inventors: Sento Ino, Tokyo; Masahiko Tamura, Ichihara; Osamu Itoh, Sodegaura, all of (JP)

(73) Assignee: Nihon Medi-Physics Co., Ltd., Hyogo-ken (JP)

( * ) Notice: Under 35 U.S.C. 154(b), the term of this patent shall be extended for 0 days.

(21) Appl. No.: 09/266,603

(22) Filed: Mar. 11, 1999

(30) Foreign Application Priority Data

Apr. 8, 1998 (JP) .................................................. 10-095824

(51) Int. Cl.⁷ .......................... A61K 51/00; B01D 59/30; G21G 1/00
(52) U.S. Cl. ......................... 423/501; 536/18.4; 536/122; 210/685; 210/682; 423/580.2
(58) Field of Search ................................. 423/501, 580.2; 210/685, 682; 260/408, 694; 536/122, 18.4, 18.5, 124

(56) References Cited

U.S. PATENT DOCUMENTS

| 4,002,455 | * | 1/1977 | Arion ................................... | 210/685 |
| 4,006,214 | * | 2/1977 | Moser ................................... | 210/685 |
| 4,853,130 | * | 8/1989 | D'Angelo et al. .................... | 210/682 |
| 4,877,558 | * | 10/1989 | Morioka et al. ...................... | 210/682 |

FOREIGN PATENT DOCUMENTS 7-232915   9/1995   (JP) .

OTHER PUBLICATIONS

"ion–exchange reaction" Encyclopedia Britannica Online. <http://www.search.eb.com/bol/topic?eu=118752&sctn=3>, Jan. 2000.*

David J. Schlyer et al, Separation of [18F] Fluoride from [18O] Water Using Anion Exchange Resin, Nov. 8, 1989, 531–533.

K. Hamacher et al, Computer–aided Synthesis (CAS) of No–carrier–added 2-[18F] Fluoro–2–deoxy–D–glucose: an Efficient Automated System for the Aminopolyether–supported Nucleophilic Fluorination, Mar. 27, 1989, pp. 49–55.

* cited by examiner

Primary Examiner—NgocYen Nguyen
(74) Attorney, Agent, or Firm—Sughrue, Mion, Zinn, Macpeak & Seas, PLLC

(57) ABSTRACT

The present invention provides a method for preparing [F-18]-fluoride ion which comprises the step of bringing [O-18]-enriched water containing [F-18]-fluoride ion formed by proton irradiation of [O-18]-enriched water into contact with a strongly acidic cation exchange resin to remove impurity cations, the step of then bringing the [O-18]-enriched water containing [F-18]-fluoride ion treated above into contact with a weakly basic anion exchange resin to make [F-18]-fluoride ion adsorbed to the resin and, along therewith, to recover the [O-18]-enriched water which has passed through the resin, and the step of eluting and collecting the [F-18]-fluoride ion adsorbed to the weakly basic anion exchange resin. According to the method for preparing [F-18]-fluoride ion of the present invention, [F-18]-fluoride ion can be collected at a high collection efficiency even from a larger amount (about 2 ml or more) of [O-18]-enriched water containing [F-18]-fluoride ion than the amount in prior method, and moreover expensive [O-18]-enriched water can be recovered and reused in the preparation of [F-18]-fluoride ion.

15 Claims, No Drawings

METHOD FOR PREPARING [F-18-]FLUORIDE ION

BACKGROUND OF THE INVENTION

1. Field of the Invention

The present invention relates to a method for preparing [F-18]-fluoride ion used for producing radiofluorinated organic compounds.

2. Related Art Statement

Radiofluorinated organic compounds are used in position emission tomography (PET), one of the medical diagnostic imaging technologies.

Currently, most radiofluorinated organic compounds are produced by organic chemical reactions of their precursors with [F-18]-fluoride ion. [F-18]-fluoride ion is formed by proton irradiation of [O-18]enriched water as target and obtained in the form of [O-18]-enriched water containing [F-18]-fluoride ion. To use the [F-18]-fluoride ion thus formed for labelling organic compounds, it is necessary to concentrate and separate [F-18]-fluoride ion from the [O-18]-enriched water containing [F-18]-fluoride ion obtained above. Furthermore, since [O-18]-enriched water is very expensive, it is desirable to recover and reuse [O-18]-enriched water after [F-18]-fluoride ion has been concentrated and separated therefrom.

A method of concentrating and separating [F18]-fluoride ion with the object of recovering and reusing [O-18]-enriched water has been already reported in the literature.

Schlyer et al. (Appl. Radiat. Isot., Vol. 41, No. 6, pp. 531–533 (1990)) reported that [O-18]-enriched water containing [F-18]-fluoride ion (about 0.5 ml) is brought into contact with a strongly basic anion exchange resin (hydroxyl form or carbonate form) to make [F-18]-fluoride ion adsorbed to the resin and, along therewith, to recover the [O-18]-enriched water which has passed through the resin and then the [F-18]-fluoride ion adsorbed to the strongly basic anion exchange resin is eluted with an aqueous solution of cesium carbonate or potassium carbonate, so that [F-18]-fluoride ion can be concentrated and separated at a collection efficiency of 95% or more. Hamacher et al. (Appl. Radiat. Isot., Vol. 41, No. 1, pp. 49–55 (1990)) reported that from about 2 ml of [O-18]-enriched water containing [F-18]-fluoride ion, in the same manner as above, [F-18]-fluoride ion can be concentrated and separated at a collection efficiency of 95% or more.

In the above-mentioned method, however, the recovered [O-18]-enriched water contains cations etc. as impurities, so that purification by distillation or the like is necessary to reuse the recovered [O-18]-enriched water for preparing radioactive fluoride ion.

On the other hand, with the increase of demand for radiofluorinated organic compounds, an increase in the production of [F-18]-fluoride ion has become necessary. Consequently, an increase in the amount of [O-18]-enriched water used in each production of [F-18]-fluoride ion is eagerly desired.

When it is intended, according to the method described above, to concentrate and separate [F-18]-fluoride ion from the larger amount of [O-18]-enriched water containing [F-18]-fluoride ion than that (about 2 ml) already reported in the literature, it may be assumed that the intention can be attained simply by increasing the amount of the resin. However, an increase in the amount of the resin makes it necessary to use an excess of aqueous basic solution as the eluent in eluting the adsorbed [F-18]-fluoride ion; this not only hinders the labelling reaction of organic compounds with the eluted [F-18]-fluoride ion but also is liable to lead to an increase in an amount of contamination with non-radioactive impurities.

OBJECT AND SUMMARY OF THE INVENTION

In view of the situations, the object of the present invention is to provide a method for preparing [F-18]-fluoride ion used for producing radiofluorinated organic compounds according to which [F-18]-fluoride ion can be collected at a high efficiency from a larger amount (about 2 ml or more) of [O-18]-enriched water containing [F-18]-fluoride ion than the amount in the prior method without increasing the amount of the resin and, at the same time, [O-18]-enriched water reusable for preparation of [F-18]-fluoride ion can be recovered without subjecting to any purification such as distillation.

DETAILED DESCRIPTION OF THE INVENTION

According to the present invention, there is provided a method for preparing [F-18]-fluoride ion used for producing radiofluorinated organic compounds which comprises the step of bringing [O-18]-enriched water containing [F-18]-fluoride ion formed by proton irradiation of [O-18]-enriched water into contact with a strongly acidic cation exchange resin to remove impurity cations, the step of then bringing the [O-18]-enriched water containing [F-18]-fluoride ion treated above into contact with a weakly basic anion exchange resin to make [F-18]-fluoride ion adsorbed to the resin and, along therewith, to recover the [O-18]-enriched water which has passed through the resin, and the step of eluting and collecting the [F-18]-fluoride ion adsorbed to the weakly basic anion exchange resin.

As compared with the prior method of concentrating and separating [F-18]-fluoride ion from [O-18]-enriched water containing [F-18]-fluoride ion by using a strongly basic anion exchange resin, which method shows a low collection efficiency, the method for preparing [F-18]-fluoride ion according to the present invention makes it possible to prepare [F-18]-fluoride ion at a high collection efficiency even from a larger amount (about 2 ml or more) of [O-18]-enriched water containing [F-18]-fluoride ion than previously.

In the prior method, moreover, a purification operation, such as distillation, is necessary for reusing the recovered [O-18]-enriched water for preparing [F-18]-fluoride ion. According to the present invention, on the other hand, since impurity cations are removed by the treatment with the strongly acidic cation exchange resin as the preliminary step for making [F-18]-fluoride ion adsorbed to the weakly basic anion exchange resin, the recovered [O-18]-enriched water can be reused without purification.

Therefore, according to the present invention, [O-18]-enriched water, which is very expensive, can be reused while the loss of the water is suppressed to the minimum.

The [O-18]-enriched water used in the present invention is a water in which 99.7% of oxygen atoms constituting water molecules consist of an oxygen isotope of mass number 18. Proton irradiation of the water forms [F-18]-fluoride ion, which are obtained in the form of anion contained in [O-18]-enriched water.

In the proton irradiation of [O-18]-enriched water, the water is placed in a target box made of metal, such as stainless steel or silver, so that the irradiated water contains cations as impurities which have dissolved out of the target box. When the impurity cations form salts with fluoride ions, it is difficult to adsorb [F-18]-fluoride ion with a weakly basic anion exchange resin. Further, when impurity cations are present as a contaminant in the recovered [O-18]-enriched water obtained after concentration and separation of [F-18]-fluoride ion, the [O-18]-enriched water cannot be reused for the preparation of [F-18]-fluoride ion unless having been subjected to purification, such as distillation.

The present inventors have succeeded in solving the above-mentioned problems by bringing [O-18]-enriched water containing [F-18]-fluoride ion into contact with a strongly acidic cation exchange resin and thereby removing impurity cations therefrom.

The strongly acidic cation exchange resin used in the present invention is preferably a compound represented by the following formula (I)

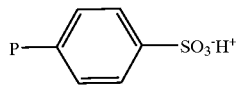

(I)

wherein P represents a styrene-divinylbenzene copolymer. The resin may be used either in the state of resin particles filled in a column or in the form of resin membrane.

The strongly acidic cation exchange resins which are commercially available may be applicable to this purpose. However, since commercial products are supplied in the form of sodium salt, they are activated, when used in the present invention, for example by the following method.

First, about 5 g of a strongly acidic cation exchange resin (e.g., AG50W X8, a trade name, mfd. by Bio-Rad Lab Inc., 100–200 mesh, Na form) is filled in an appropriate plastics column. Then about 50 ml of 4 N aqueous hydrochloric acid solution is passed through the column to convert the ion form of the resin from the sodium form to the hydrogen form. Thereafter, the resin in the column is washed with deionized water until the pH of the eluate becomes neutral.

The strongly acidic cation exchange resin thus activated dissociates in a weakly acidic solution as well as alkaline solution, and exhibits ion exchanging ability. Therefore, when in the present invention an approximately neutral [O-18]-enriched water containing [F-18]-fluoride ion is brought into contact with the activated resin, impurity cations which have formed salts with [F-18]-fluoride ion are exchanged with hydrogen ion of the resin, whereby [O-18]-enriched water containing [F-18]-hydrogen fluoride is formed.

Then the [O-18]-enriched water containing [F-18]-hydrogen fluoride is brought into contact with a weakly basic anion exchange resin to make [F-18]-fluoride ion adsorbed to the resin and, along therewith, to recover [O-18]-enriched water which has passed through the resin. The weakly basic anion exchange resin used in this step is preferably a compound represented by the following formula (II), wherein RI and $R_2$ are each an alkyl group of 1–4 carbon atoms, preferably the methyl group. In using the resin, the resin may be either in the state of resin particles filled in a column or in the form of resin membrane.

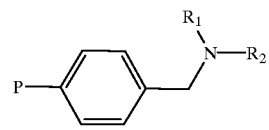

(II)

wherein P represents a styrene-divinylbenzene copolymer, and $R_1$ and $R_2$ each independently represent the methyl group, ethyl group, propyl group or butyl group.

The weakly basic anion exchange resins which are commercially available may be applicable to this purpose, but when used in the present invention they are activated for example by the following method.

First, about 5 g of a weakly basic anion exchange resin (e.g., AG3 X4, a trade name, mfd. by Bio-Rad Lab Inc., 100–200 mesh, free base form) is filled in an appropriate plastics column. Then about 30 ml of an aqueous potassium carbonate solution (about 50 g/l) is passed through the column to remove ions (mainly chloride ions) remaining in the resin. Thereafter the resin in the column is washed with deionized water until the pH of the eluate becomes neutral.

The resin thus activated can exchange anions only in neutral or acidic solutions, and can decompose and exchange mineral acids, weakly basic salts, etc. Therefore, when an approximately neutral [O-18]-enriched water containing [F-18]-hydrogen fluoride is brought into contact with the activated resin, [F-18]-fluoride ion is adsorbed onto the resin and [O-18]-enriched water which has passed through the resin is recovered; thus [F-18]-fluoride ion and [O-18]-enriched water can be separated from each other.

Since the [O-18]-enriched water thus recovered has been free of impurity cations, it can be reused in the preparation of [F-18]-fluoride ion without further purification. In the prior technology, on the other hand, in reusing the recovered [O-18]-enriched water for preparing [F-18]-fluoride ion, impurity cations contaminated in the recovered [O-18]-enriched water must be removed and hence a purification, such as distillation, is necessary. Such a purification is accompanied by the loss of valuable [O-18]-enriched water and requires additional process steps, so that the prior technology is not suitable for a recovery method.

The [F-18]-fluoride ion adsorbed to the weakly basic anion exchange resin is eluted and collected to be used in the production of radiofluorinated organic compounds. The eluent used at this time is preferably an aqueous solution of an alkali metal carbonate, more preferably an aqueous potassium carbonate solution.

Since the preparation of radiofluorinated organic compounds are performed in an organic solvent, the [F-18]-fluoride ion eluted in the form of water-soluble alkali metal salt, which are slightly soluble in organic solvents, cannot be used for the labelling reaction. When a phase transfer catalyst is added to an aqueous solution containing eluted [F-18]-fluoride ion and the resulting mixture is evaporated to dryness, the [F-18]-fluoride ion are activated and can be used for the labelling reaction.

The phase transfer catalyst used herein may be an aminopolyether, preferably Kryptofix® 2.2.2. An aminopolyether encloses alkali metal ions forming salts with [F-18]-fluoride ion to form a clathrate complex and thereby makes the [F-18]-fluoride ion soluble in organic solvents.

A substrate to be labelled with [F-18]-fluoride ion is added to the dried residue containing [F-18]-fluoride ion thus activated and is allowed to undergo a nucleophilic substitution reaction, and then the reaction product is purified with an alumina column or the like, whereby the objective radiofluorinated organic compound is obtained.

The radiofluorinated organic compounds prepared through the steps described above are used in the positron emission tomography, one of the medical diagnostic imaging technologies. Specific examples of the compound include brain receptor-binding compounds, such as [F-18]-L-6-fluorodopa and [F-18]-R-4-fluorodeprenil, and hormone-like compounds, such as [F-18]-fluoronorepinephrine and [F-18]-fluorodopamine. Among them, [F-18]-2-fluoro-2-deoxy-D-glucose is widely used as the diagnostic imaging agent for tumors, circulatory diseases and brain diseases at present in clinical sites.

PREFERRED EMBODIMENTS OF THE INVENTION

The present invention is described in detail below with reference to Examples.

EXAMPLE 1

Preparation of [F-18]-fluoride ion

The preparation of [F-18]-fluoride ion from [O-18]-enriched water containing [F-18]-fluoride ion produced by proton irradiation of [O-18]-enriched water was carried out with varied amount of the [O-18]-enriched water.

A cation exchange resin column was prepared by filling an activated strongly acidic cation exchange resin (AG50W X8, a trade name, mfd. by Bio-Rad Lab Inc., 100–200 mesh) in a plastics column. Separately, an anion exchange resin column was prepared by filling an activated weakly basic anion exchange resin (AG3 X4, a trade name, mfd. by Bio-Rad Lab Inc., 100–200 mesh) in a plastics column. Thereafter, [O-18]-enriched water containing [F-18]-fluoride ion produced by proton irradiation of [O-18]-enriched water was brought into contact with the cation exchange resin column and then with the anion exchange resin column each prepared above, to make [F-18]-fluoride ion adsorbed to the weakly basic cation exchange resin and to recover the [O-18]-enriched water which had passed through the columns.

The collection efficiency for [F-18]-fluoride ion was determined from the radioactivity of the [O-18]-enriched water containing [F-18]-fluoride ion before being brought into contact with the cation exchange resin column and the radioactivity of the [F-18]-fluoride ion adsorbed onto the weakly basic anion exchange resin. The results thus obtained with respective experiments and the conditions of the experiments are shown in Table 1.

TABLE 1

Preparation of [F-18]-fluoride ion

|  | Experiment 1 | Experiment 2 | Experiment 3 | Experiment 4 |
|---|---|---|---|---|
| [0–18]-enriched water containing [F-18]-fluoride ion (ml) | 12.2 | 30.6 | 90.1 | 151 |
| Radioactivity at the end of proton irradiation (GBq) | 136.2 | 162.9 | 86.5 | 2.64 |
| Strongly acidic cation exchange resin (ml) | 1 | 1 | 1 | 1 |
| Cation exchange resin column diameter (mm) | 5 | 5 | 5 | 5 |

TABLE 1-continued

Preparation of [F-18]-fluoride ion

|  | Experiment 1 | Experiment 2 | Experiment 3 | Experiment 4 |
|---|---|---|---|---|
| Weakly basic anion exchange resin (ml) | 0.06 | 0.06 | 0.4 | 0.4 |
| Anion exchange resin column diameter (mm) | 2 | 2 | 4.8 | 4.8 |
| Collection efficiency for [F-18]-fluoride ion (%) | 97.0 | 99.6 | 97.3 | 78.2 |

COMPARATIVE EXAMPLE 1

Preparation of [F-18]-fluoride ion by prior method

In the prior method for preparation of [F-18]-fluoride ion, wherein [F-18]-fluoride ion is concentrated and separated by bringing [O-18]-enriched water containing [F-18]-fluoride ion into contact with a strongly basic anion exchange resin, the collection efficiency for [F-18]-fluoride ion decreases when the amount of the [O-18]-enriched water containing [F-18]-flouride ion exceeds about 2 ml. To confirm the above-mentioned conclusion, [F-18]-fluoride ion was prepared according to the method described by K. Hamacher et al. (Appl. Radiat. Isot., Vol. 41, No. 1, pp. 49–55, 1990).

First, 0.4 ml of a strongly basic anion exchange resin (AG1 X8, a trade name, mfd. by Bio-Rad Lab Inc., 100–200 mesh, Cl form) was filled in a column made from a 1-ml disposable syringe (made of plastics), and then 10 ml of an aqueous potassium carbonate solution (46 g/l) was passed through the column to convert the ion form of the resin from the chloride form into the carbonate form. Then the resin in the column was washed with deionized water until the pH of the eluate became neutral to activate the strongly basic anion exchange resin. Thereafter the activated strongly basic anion exchange resin was filled in a plastics column to prepare an ion exchange resin column. [O-18]-enriched water containing [F-18]-fluoride ion was brought into contact with the ion exchange resin column prepared above to make [F-18]-fluoride ion adsorbed onto the strongly basic anion exchange resin and to recover the [O-18]-enriched water which had passed through the resin.

The collection efficiency for [F-18]-fluoride ion was determined from the radioactivity of the [O-18]-enriched water containing [F-18]-fluoride ion before being brought into contact with the ion exchange resin column and the radioactivity of the [F-18]-fluoride ion adsorbed onto the strongly basic anion exchange resin. The results thus obtained with respective experiments and the conditions of the experiments are shown in Table 2.

TABLE 2

Preparation of [F-18]-fluoride ion by prior method

|  | Comparative Experiment 1 | Comparative Experiment 2 |
|---|---|---|
| [0–18]-enriched water containing [F-18]-fluoride ion (ml) | 2.3 | 28.5 |
| Radioactivity at the end of proton irradiation (GBq) | 6.35 | 86.5 |
| strongly basic anion exchange resin (ml) | 0.06 | 0.06 |

TABLE 2-continued

Preparation of [F-18]-fluoride ion by prior method

|  | Comparative Experiment 1 | Comparative Experiment 2 |
|---|---|---|
| Ion exchange resin column diameter (mm) | 2 | 2 |
| Collection efficiency for [F-18]-fluoride ion (%) | 92.1 | 28.0 |

EXAMPLE 2

Preparation of [F-18]-fluoride Ion by Reusing Recovered [O-18]-enriched Water The [O-18]-enriched water recovered in the process of preparation of [F-18]-fluoride ion according to the present invention can be reused in the preparation of [F-18]-fluoride ion without further purification. This was confirmed by repeated actual preparation of [F-18 ]-2-fluoro-2-deoxy-D-glucose.

The [O-18]-enriched water recovered in the [F-18]-fluoride ion preparation of the previous time was subjected without any purification to proton irradiation to form [O-18]-enriched water containing [F-18]-fluoride ion. The [O-18]-enriched water thus produced was brought into contact with a strongly acidic cation exchange resin and then with a weakly basic anion exchange resin to make [F-18]-fluoride ion adsorbed onto the weakly basic anion exchange resin and to recover the [O-18]-enriched water which had passed through the resin, thus separating the [F-18]-fluoride ion and [O-18]-enriched water each other.

Then the [F-18]-fluoride ion adsorbed onto the weakly basic anion exchange resin was eluted with 2 ml of an aqueous solution containing 4.6 mg of potassium carbonate. Thereafter, 80 mg of an aminopolyether (Kryptofix® 2.2.2.) was added as a phase transfer catalyst to the eluate and the resulting mixture was evaporated to dryness to activate the [F-18]-fluoride ion. To the residue thus obtained was added a solution of 50 mg of a substrate (1,3,4,6-tetra-O-acetyl-2-O-trifluoromethanesulfonyl-β-D-mannopyranose) dissolved in 1 ml of acetonitrile, and the resulting mixture was allowed to undergo a nucleophilic substitution reaction at 105° C. for 5 minutes. Then the solvent was distilled off, 12 ml of diethyl ether was added to the residue to dissolve the radiofluorinated substrate, the resulting solution was purified with a silica gel column (Sep-Pak silica, a trade name, mfd. by Waters Co.) and was immediately transferred to the next reaction vessel. Then the solvent was distilled off, 4 ml of 0.7N hydrochloric acid was added to the residue, and the resulting mixture was allowed to undergo hydrolysis at 130° C. for 15 minutes. The product thus obtained was purified by passing it through an ion retardation resin (AG11 A8, a trade name, mfd. by Bio-Rad Lab Inc.), an alumina column (Sep-Pak Alumina N, a trade name, mfd. by Waters Co.) and an octadecyl column (Sep-Pak C18, a trade name, mfd. by Waters Co.) in the above-mentioned order to obtain the objective compound, [F-18]-2-fluoro2-deoxy-D-glucose.

The above-mentioned series of preparation was repeated 15 times and the results obtained are shown in Table 3.

TABLE 3

Preparation of [F-18]-2-fluoro-2-deoxy-D-glucose

|  | Collection efficiency (%) | Labelling efficiency (%) | Yield (%) |
|---|---|---|---|
| 1 | 98.8 | 70.7 | 37.0 |
| 2 | 98.3 | 76.9 | 46.5 |
| 3 | 98.4 | 78.5 | 45.4 |
| 4 | 98.0 | 64.6 | 40.5 |
| 5 | 96.8 | 69.6 | 45.0 |
| 6 | 98.0 | 61.8 | 37.8 |
| 7 | 96.6 | 71.6 | 43.5 |
| 8 | 96.7 | 60.7 | 34.9 |
| 9 | 98.0 | 73.7 | 42.5 |
| 10 | 98.1 | 77.9 | 48.4 |
| 11 | 98.0 | 75.9 | 47.7 |
| 12 | 97.9 | 67.5 | 32.8 |
| 13 | 98.0 | 77.5 | 47.6 |
| 14 | 87.7 | 82.2 | 47.8 |
| 15 | 96.4 | 87.8 | 47.9 |
| Average ± standard deviation | 97.0 ± 2.6 | 73.1 ± 7.6 | 43.0 ± 5.2 |

In Table 3, the "collection efficiency" represents the percentage of the radioactivity of [F-18]-fluoride ion adsorbed onto the weakly basic anion exchange resin relative to the radioactivity of the [O-18]-enriched water containing [F-18]-fluoride ion before being brought into contact with the strongly acidic cation exchange resin. The "labelling efficiency" represents the percentage of the radioactivity of the [F-18]-1,3,4,6-tetra-O-acetyl-2-fluoro-2-deoxy-D-glucose relative to the radioactivity of the [F-18]-fluoride ion activated by addition of a phase transfer catalyst and subsequent evaporation to dryness. The "yield" represents the percentage of the radioactivity of the [F-18]-2-fluoro-2-deoxy-D-glucose relative to the radioactivity of the [O-18]-enriched water containing [F-18]-fluoride ion.

From the results shown in Table 3, it was revealed that even when [O-18]-enriched water recovered in the process of preparing [F-18]-fluoride ion was repeatedly used for the preparation of [F-18]-fluoride ion without being subjected to any purification, [F-18]-fluoride ion was obtained at a collection efficiency of average 97%. Further, it was confirmed that when the [F-18]-fluoride ion thus obtained at each time of preparation was used for preparing a radiofluorinated organic compound, the objective compound could be prepared each time in an approximately equal yield.

What is claimed is:

1. A method for preparing [F-18]-fluoride ion for labelling used for producing radiofluorinated organic compounds which comprises the step of bringing [O-18]-enriched water containing [F-18]-fluoride ion formed by proton irradiation of [O-18]-enriched water into contact with a strongly acidic cation exchange resin to remove impurity cations, the step of then bringing the [O-18]-enriched water containing [F-18]-fluoride ion treated above into contact with a weakly basic anion exchange resin to make [F-18]-fluoride ion adsorbed to the weakly basic anion exchange resin and, along therewith, to recover the [O-18]-enriched water which has passed through the weakly basic anion exchange resin, and the step of eluting and collecting the [F-18]-fluoride ion adsorbed to the weakly basic anion exchange resin.

2. The method for preparing [F-18]-fluoride ion according to claim 1, wherein the strongly acidic cation exchange resin is a compound represented by the formula

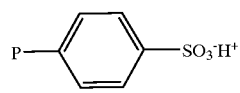

wherein P represents a styrene-divinylbenzene copolymer.

3. The method for preparing [F-18]-fluoride ion according to claim 1 or 2, wherein the strongly acidic cation exchange resin is used in the state of resin particles filled in a column.

4. The method for preparing [F-18]-fluoride ion according to claim 1 or 2, wherein the strongly acidic cation exchange resin is used in the form of membrane.

5. The method for preparing [F-18]-fluoride ion according to claim 1 or 2, wherein the weakly basic anion exchange resin is a compound represented by the formula (II)

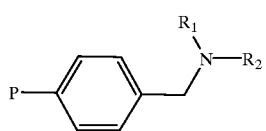

wherein P represents a styrene-divinylbenzene copolymer, and $R_1$ and $R_2$ each independently represent the methyl group, ethyl group, propyl group or butyl group.

6. The method for preparing [F-18]-fluoride ion according to claim 1 or 2, wherein the weakly basic anion exchange resin is used in the state of resin particles filled in a column.

7. The method for preparing [F-18]-fluoride ion according to claim 1 or 2, wherein the weakly basic anion exchange resin is used in the form of membrane.

8. The method for preparing [F-18]-fluoride ion according to claim 1, wherein in the step of eluting and collecting the [F-18]-fluoride ion adsorbed to the weakly basic anion exchange resin, the eluent is an aqueous solution of an alkali metal carbonate.

9. The method for preparing [F-18]-fluoride ion according to claim 1, wherein in the step of eluting and collecting the [F-18]-fluoride ion adsorbed to the weakly basic anion exchange resin, the eluent is an aqueous potassium carbonate solution.

10. The method for preparing [F-18]-fluoride ion according to claim 1 or 2, wherein the recovered [O-18]-enriched water is reused for the preparation of [F-18]-fluoride ion.

11. The method for preparing [F-18]-fluoride ion according to claim 5, wherein the weakly basic anion exchange resin is used in the state of resin particles filled in a column.

12. The method for preparing [F-18]-fluoride ion according to claim 5 wherein the weakly basic anion exchange resin is used in the form of membrane.

13. The method for preparing [F-18]-fluoride ion according to claim 5, wherein in the step of eluting and collecting the [F-18]-fluoride ion adsorbed to the weakly basic anion exchange resin, the eluent is an aqueous solution of an alkali metal carbonate.

14. The method for preparing [F-18]-fluoride ion according to claim 5, wherein in the step of eluting and collecting the [F-18]-fluoride ion adsorbed to the weakly basic anion exchange resin, the eluent is an aqueous potassium carbonate solution.

15. The method for preparing [F-18]-fluoride ion according to claim 5, wherein the recovered [O-18]-enriched water is reused for the preparation of [F-18]-fluoride ion.

* * * * *